(12) United States Patent
Styczynski et al.

(10) Patent No.: US 7,261,878 B2
(45) Date of Patent: *Aug. 28, 2007

(54) REDUCTION OF HAIR GROWTH

(75) Inventors: Peter Styczynski, Wrentham, MA (US); Gurpreet S. Ahluwalia, Potomac, MD (US); Douglas Shander, Acton, MA (US)

(73) Assignee: The Gillette Company, Boston, MA (US)

( * ) Notice: Subject to any disclaimer, the term of this patent is extended or adjusted under 35 U.S.C. 154(b) by 248 days.

This patent is subject to a terminal disclaimer.

(21) Appl. No.: 10/198,456

(22) Filed: Jul. 17, 2002

(65) Prior Publication Data

US 2003/0035818 A1 Feb. 20, 2003

Related U.S. Application Data

(60) Provisional application No. 60/311,605, filed on Aug. 10, 2001.

(51) Int. Cl.
 *A61K 8/00* (2006.01)
 *A61K 8/18* (2006.01)
 *A61K 8/02* (2006.01)
 *A61K 31/195* (2006.01)

(52) U.S. Cl. ..................... 424/70.1; 424/401; 514/564; 514/938

(58) Field of Classification Search ................ 424/401, 424/70.1; 514/564, 938
See application file for complete search history.

(56) References Cited

U.S. PATENT DOCUMENTS

| | | | |
|---|---|---|---|
| 3,426,137 A | 2/1969 | Philpitt et al. | |
| 4,039,669 A | 8/1977 | Beyler et al. | |
| 4,139,638 A | 2/1979 | Neri et al. | |
| 4,161,540 A | 7/1979 | Neri et al. | |
| 4,191,775 A | 3/1980 | Glen | |
| 4,269,831 A | 5/1981 | Ferrari et al. | |
| 4,370,315 A | 1/1983 | Greff et al. | |
| 4,439,432 A | 3/1984 | Peat | |
| 4,508,714 A | 4/1985 | Cecic et al. | |
| 4,517,175 A | 5/1985 | Iwabuchi et al. | |
| 4,720,489 A | 1/1988 | Shander | |
| 4,885,289 A | 12/1989 | Breuer et al. | |
| 4,935,231 A | 6/1990 | Pigiet | |
| 5,095,007 A | 3/1992 | Ahluwalia | |
| 5,096,911 A | 3/1992 | Ahluwalia et al. | |
| 5,132,293 A | 7/1992 | Shander et al. | |
| 5,143,925 A | 9/1992 | Shander et al. | |
| 5,189,212 A | 2/1993 | Ruenitz | |
| 5,271,942 A | 12/1993 | Heverhagen | |
| 5,300,284 A | 4/1994 | Wiechers et al. | |
| 5,328,686 A | 7/1994 | Shander et al. | |
| 5,362,748 A | 11/1994 | Schwen et al. | |
| 5,364,885 A | 11/1994 | Ahluwalia et al. | |
| 5,411,991 A | 5/1995 | Shander et al. | |
| 5,444,090 A | 8/1995 | Ahluwalia | |
| 5,455,234 A | 10/1995 | Ahluwalia et al. | |
| 5,468,476 A | 11/1995 | Ahluwalia et al. | |
| 5,474,763 A | 12/1995 | Shander et al. | |
| 5,554,608 A | 9/1996 | Ahluwalia et al. | |
| 5,645,825 A | 7/1997 | Hillebrand et al. | |
| 5,648,394 A | 7/1997 | Boxall et al. | |
| 5,652,273 A | 7/1997 | Henry et al. | |
| 5,674,477 A | 10/1997 | Ahluwalia | |
| 5,728,736 A | 3/1998 | Shander et al. | |
| 5,776,442 A | 7/1998 | Ahluwalia | |
| 5,824,665 A | 10/1998 | Henry et al. | |
| 5,840,752 A | 11/1998 | Henry et al. | |
| 5,908,867 A | 6/1999 | Henry et al. | |
| 5,939,458 A | 8/1999 | Henry et al. | |
| 5,958,946 A | 9/1999 | Styczynski et al. | |
| 5,962,466 A | 10/1999 | Styczynski et al. | |
| 6,020,006 A | 2/2000 | Styczynski et al. | |
| 6,037,326 A | 3/2000 | Styczynski et al. | |
| 6,060,471 A | 5/2000 | Styczynski et al. | |
| 6,093,748 A | 7/2000 | Ahluwalia et al. | |
| 6,121,269 A | 9/2000 | Henry et al. | |
| 6,218,435 B1 | 4/2001 | Henry et al. | |
| 6,235,737 B1 | 5/2001 | Styczynski et al. | |
| 6,239,170 B1 | 5/2001 | Ahluwalia et al. | |
| 6,248,751 B1 | 6/2001 | Ahluwalia et al. | |
| 6,284,234 B1 | 9/2001 | Niemiec et al. | |

(Continued)

FOREIGN PATENT DOCUMENTS

EP    0 413 528 B1    8/1990

(Continued)

OTHER PUBLICATIONS

Botchkarev et al., "A New Role for Neurotrophin-3", *American Journal of Pathology*, vol. 153, pp. 785-799, 1998.

(Continued)

*Primary Examiner*—Sreeni Padmanabhan
*Assistant Examiner*—Marina Lamm
(74) *Attorney, Agent, or Firm*—Fish & Richardson P.C.

(57) ABSTRACT

A topical composition useful for reducing in hair growth includes α-difluoromethylornithine and a dermatologically acceptable vehicle comprising at least 4% by weight of a polyoxyethylene ether having the chemical formula $R(OCH_2CH_2)_bOH$, where R is a saturated or unsaturated alkyl group including from 6 to 22 carbon atoms and b is from 2 to 200.

22 Claims, No Drawings

U.S. PATENT DOCUMENTS

| | | | |
|---|---|---|---|
| 6,299,865 | B1 | 10/2001 | Styczynski et al. |
| 6,511,655 | B1 * | 1/2003 | Muller et al. ............... 424/59 |
| 6,743,822 | B2 * | 6/2004 | Styczynski et al. ......... 514/564 |
| 2002/0045663 | A1 | 4/2002 | Levenson et al. |
| 2003/0053973 | A1 | 3/2003 | Chou et al. |

FOREIGN PATENT DOCUMENTS

| | | |
|---|---|---|
| EP | 0 532 219 A2 | 9/1992 |
| GB | 1 458 349 | 11/1995 |
| WO | WO98/02134 | 1/1998 |
| WO | WO 03/0152729 | 2/2003 |
| WO | WO 03/020209 A2 | 3/2003 |

OTHER PUBLICATIONS

Botchkarev et al., "Neurotrophin-3 Involvement in the Regulation of Hair Follicle Morphogenesis", *The Journal of Investigative Dermatology*, vol. 111, No. 2, pp. 279-285, 1998.

Hoffmann et al., "Interleukin-1 β-Induced Inhibition of Hair Growth in Vitro Is Mediated by Cyclic AMP", *The Journal of Investigative Dermatology*, vol. 108, pp. 40-42, 1997.

Messenger, Andrew G., "The Control of Hair Growth: An Overview", *The Journal of Investigative Dermatology*, vol. 101, No. 1, pp. 4s-9s, 1993.

Weinberg et al., "Reconstitution of Hair Follicle Development In Vitro: Determination of Follicle Formation, Hair Growth, and Hair Quality by Dermal Cells", *The Journal of Investigative Dermatology*, vol. 100, pp. 229-236, 1993.

Ebling, F. John G., "The Biology of Hair", *Dermatologic Clinics*, vol. 5, No. 3, pp. 467-481, 1987.

Hattori et al., "Biochemical Analysis of Hair Growth From the Aspects of Aging and Enzyme Activities", *The Journal of Dermatology*, vol. 10, pp. 45-54, 1983.

Adachi et al., "Human Hair Follicles: Metabolism and Control Mechanisms", *Journal of the Society of Cosmetic Chemists*, vol. 21, No. 13, pp. 901-924, 1970.

* cited by examiner

REDUCTION OF HAIR GROWTH

This application claims the benefit of prior U.S. provisional application 60/311,605, filed Aug. 10, 2001.

BACKGROUND

The invention relates to reducing hair growth in mammals, particularly for cosmetic purposes.

A main function of mammalian hair is to provide environmental protection. However, that function has largely been lost in humans, in whom hair is kept or removed from various parts of the body essentially for cosmetic reasons. For example, it is generally preferred to have hair on the scalp but not on the face.

Various procedures have been employed to remove unwanted hair, including shaving, electrolysis, depilatory creams or lotions, waxing, plucking, and therapeutic antiandrogens. These conventional procedures generally have drawbacks associated with them. Shaving, for instance, can cause nicks and cuts, and can leave a perception of an increase in the rate of hair regrowth. Shaving also can leave an undesirable stubble. Electrolysis, on the other hand, can keep a treated area free of hair for prolonged periods of time, but can be expensive, painful, and sometimes leaves scarring. Depilatory creams, though very effective, typically are not recommended for frequent use due to their high irritancy potential. Waxing and plucking can cause pain, discomfort, and poor removal of short hair. Finally, antiandrogens—which have been used to treat female hirsutism—can have unwanted side effects.

It has previously been disclosed that the rate and character of hair growth can be altered by applying to the skin inhibitors of certain enzymes. These inhibitors include inhibitors of 5-alpha reductase, ornithine decarboxylase, S-adenosylmethionine decarboxylase, gamma-glutamyl transpeptidase, and transglutaminase. See, for example, Breuer et al., U.S. Pat. No. 4,885,289; Shander, U.S. Pat. No. 4,720,489; Ahluwalia, U.S. Pat. No. 5,095,007; Ahluwalia et al., U.S. Pat. No. 5,096,911; and Shander et al., U.S. Pat. No. 5,132,293.

α-Difluoromethylornithine (DFMO) is an irreversible inhibitor of ornithine decarboxylase (ODC), a rate-limiting enzyme in the de novo biosynthesis of putrescine, spermidine, and spermine. The role of these polyamines in cellular proliferation is not yet well understood. However, they seem to play a role in the synthesis and/or regulation of DNA, RNA and proteins. High levels of ODC and polyamines are found in cancer and other cell types that have high proliferation rates.

DFMO binds the ODC active site as a substrate. The bound DFMO is then decarboxylated and converted to a reactive intermediate that forms a covalent bond with the enzyme, thus preventing the natural substrate ornithine from binding to the enzyme. Cellular inhibition of ODC by DFMO causes a marked reduction in putrescine and spermidine and a variable reduction in spermine, depending on the length of treatment and the cell type. Generally, in order for DFMO to cause significant antiproliferative effects, the inhibition of polyamine synthesis must be maintained by continuous inhibitory levels of DFMO because the half-life of ODC is about 30 min, one of the shortest of all known enzymes.

A skin preparation containing DFMO (sold under the name Vaniqa® by Bristol Myers Squibb), has recently been approved by the Food and Drug Administration (FDA) for the treatment of unwanted facial hair growth in women. Its topical administration in a cream based vehicle has been shown to reduce the rate of facial hair growth in women. Vaniqa® facial cream includes a racemic mixture of the "D-" and "L-" enantiomers of DFMO (i.e., D,L-DFMO) in the monohydrochloride form at a concentration of 13.9% by weight active (15%, as monohydrochloride monohydrate). The recommended treatment regimen for Vaniqa® is twice daily. The cream base vehicle in Vaniqa® is set out in Example 1 of U.S. Pat. No. 5,648,394, which is incorporated herein by reference. The cream vehicle includes 2.5% by weight ceteareth-20. Ceteareth-20 is a blend of two polyoxyethylene ethers of alkyl alcohols having the chemical formulas $CH_3(CH_2)_{15}(OCH_2CH_2)_b$ OH and $CH_3(CH_2)_{17}(OCH_2CH_2)_b$ OH, where b has an average value of 20.

It generally takes about eight weeks of continuous treatment before the hair growth-inhibiting efficacy of Vaniqa® cream becomes apparent. Vaniqa® cream has been shown to decrease hair growth an average of 47%. In one study, clinical successes were observed in 35% of women treated with Vaniqa® cream. These women exhibited marked improvement or complete clearance of their condition as judged by physicians scoring a decrease in visibility of facial hair and a decrease in skin darkening caused by hair. Another 35% of the women tested experienced some improvement in their condition. However, there were some women who exhibited little or no response to treatment.

Accordingly, although Vaniqa® cream is an effective product, it would be even more effective if it provided an earlier onset of hair growth inhibition (i.e., exhibited efficacy earlier than eight weeks) and/or exhibited an increased clinical success rate (i.e., exhibited efficacy in a greater percentage of users). Such improved results cannot be obtained by simply increasing the concentration of D,L-DFMO in the cream vehicle. First, increasing the concentration of D,L-DFMO above about 14% can cause increased stinging of the skin and/or can leave a residue, making it aesthetically unacceptable. Second, it is difficult to formulate compositions with an active concentration above about 15% because significantly higher concentrations of D,L-DFMO are not adequately soluble in the vehicle or destabilize the emulsion.

Molecules that are identical to each other in chemical structural formula and yet are not superimposable upon each other are enantiomers. In terms of their physiochemical properties enantiomers differ only in their ability to rotate the plane of plane-polarized light, and this property is frequently used in their designation. Those entiomers that rotate plane-polarized light to the right are termed dextrorotatory, indicated by either a (+)- or d- or D- before the name of the compound; those that rotate light to the left are termed laevorotatory indicated by a (−)- or l- or L- prefix. A racemic mixture is indicated by either a (±)- or d,l- or D,L- prefix. By another convention (or nomenclature), the R,S or the sequence rule can be used to differentiate enantiomers based on their absolute configuration. Using this system the L-DFMO corresponds to the R-DFMO, and the D-DFMO corresponds to the S-DFMO. Enantiomers are physiochemically similar in that they have similar melting points, boiling points, relative solubility, and chemical reactivity in an achiral environment. A racemate is a composite of equal molar quantities of two enantiomeric species, often referred to as the DL-form. Individual enantiomers of chiral molecules may possess different pharmacological profiles, i.e., differences in pharmacokinetics, toxicity, efficacy, etc.

SUMMARY

The present invention provides a method (typically a cosmetic method) of reducing human hair growth by applying to the skin in an amount effective to reduce hair growth a dermatologically acceptable topical composition including α-difluoromethylornithine (DFMO) and a dermatologically acceptable vehicle. The vehicle includes at least 4%, preferably at least 5% by weight, more preferably at least 6% by weight, of a polyoxyethylene ether having the chemical formula $R(OCH_2 CH_2)_b$ OH, where R is a saturated or unsaturated alkyl group including from 6 to 22 carbon atoms and b is from 2 to 200. Preferably the alkyl group includes from between 8 to 20, more preferably from 10 to 18, carbon atoms and b has an average value of from 2 to 100, more preferably from 2 to 50, most preferably from 2 to 30. The unwanted hair growth may be undesirable from a cosmetic standpoint or may result, for example, from a disease or an abnormal condition (e.g., hirsutism).

For purposes of this application, the vehicle includes all components of the composition except the DFMO. DFMO, as used herein, includes DFMO itself and pharmaceutically acceptable salts thereof.

Preferably the DFMO will comprise at least about 70% or 80%, more preferably at least about 90%, most preferably at least about 95%, L-DFMO. Ideally, the DFMO will be substantially optically pure L-DFMO. "Substantially optically pure" means that the DFMO comprises at least 98% L-DFMO. "Optically pure" L-DFMO means that the DFMO comprises essentially 100% L-DFMO.

The present invention also provides topical compositions including DFMO in an amount effective to reduce hair growth and a dermatologically acceptable vehicle including at least 4%, preferably at least 5% by weight of the polyoxyethylene ether having the chemical formula described above.

The above compositions have an enhanced efficacy relative to similar compositions having vehicles containing, for example, no or lesser amounts (e.g., 2.5% by weight) of the polyoxyethylene ether. This enhanced efficacy can manifest itself, for example, in earlier onset of hair growth inhibiting activity, greater reduction of hair growth rate, and/or greater number of subjects demonstrating reduced hair growth. Without being bound by any theory, it is believed that the polyoxyethylene ether disrupts, solubilizes and/or emulsifies the lipid component of the skin, leading to enhanced skin absorption of the DFMO.

Preferred compositions include about 0.1% to about 30%, preferably about 1% to about 20%, more preferably about 5% to about 15%, by weight of the DFMO.

Other features and advantages of the invention will be apparent from the description and from the claims.

DETAILED DESCRIPTION

The preferred composition includes substantially optically pure L-DFMO in a cosmetically and/or dermatologically acceptable vehicle including at least 5% by weight of a polyoxyethylene ether having the chemical formula $R(OCH_2CH_2)_b$ OH, where R is a saturated or unsaturated alkyl group including from 8 to 20 carbon atoms and b has an average value of from 2 to 100. The composition may be a solid, semi-solid, cream, or liquid. The composition may be, for example, a cosmetic and dermatologic product in the form of an, for example, ointment, lotion, foam, cream, gel, or solution. The composition may also be in the form of a shaving preparation or an aftershave. The vehicle itself can be inert or it can possess cosmetic, physiological and/or pharmaceutical benefits of its own.

Preferred polyoxyethylene ethers include polyoxyethylene (2) stearyl ether (steareth-2) ($R=CH_3(CH_2)_{17}$, b=2), polyoxyethylene (2) oleyl ether (oleth-2) ($R=CH_3,(CH_2)_7 CHCH(CH_2)_8$, b=2), polyoxyethylene (4) lauryl ether (laureth-4) ($R=CH_3(CH_2)_{11}$, b=4), polyoxyethylene (23) lauryl ether (laureth-23) ($R=CH_3(CH_2)_{11}$, b=23), polyoxyethylene (20) cetyl ether and polyoxyethylene (20) stearyl ether (ceteareth-20) ($R=CH_3(CH_2)_{15}$ and $CH_3(CH_2)_{17}$, b=20), and polyoxyethylene (20) stearyl ether (steareth-20) ($R=CH_3(CH_2)_{17}$, b=20).

The composition may include one or more other types of hair growth reducing agents, such as those described in U.S. Pat. No. 5,364,885 or U.S. Pat. No. 5,652,273.

The concentration of DFMO in the composition may be varied over a wide range up to a saturated solution, preferably from 0.1% to 30% by weight; the reduction of hair growth increases as the amount of DFMO applied increases per unit area of skin. The maximum amount effectively applied is limited only by the rate at which the DFMO penetrates the skin. The effective amounts may range, for example, from 10 to 3000 micrograms or more per square centimeter of skin.

Vehicles can be formulated with liquid or solid emollients, solvents, thickeners, humectants and/or powders. Emollients include, for example, stearyl alcohol, mink oil, cetyl alcohol, oleyl alcohol, isopropyl laurate, polyethylene glycol, olive oil, petroleum jelly, palmitic acid, oleic acid, and myristyl myristate. Solvents include, for example, water, ethyl alcohol, isopropanol, acetone, diethylene glycol, ethylene glycol, dimethyl sulfoxide, and dimethyl formamide.

Optically pure L-DFMO can be prepared by known methods. See, for example, U.S. Pat. No. 4,309,442; Gao et al., Ann. Pharm. Fr. 52(4):184-203 (1994); Gao et al., Ann. Pharm. Fr. 52(5):248-59 (1994); and Jacques et al., Tetrahedron Letters, 48:4617 (1971), all of which are incorporated by reference herein.

The following are examples of compositions.

EXAMPLE 1

A composition contains up to 15% by weight DFMO in a vehicle containing water 64.6%, ethanol 15.2%, propylene glycol 4.75%, dipropylene glycol 4.75%, a polyoxyethylene ether 5%, benzyl alcohol 3.8%, and propylene carbonate 1.9%. The polyoxyethylene ether may be, for example, oleth-2, steareth-2, laureth-23, or laureth-4.

EXAMPLES 2-5

Examples of DFMO formulations with polyoxyethylene ether with or without an additional penetration enhancer.

| Ingredient | Example-2 Percent (wt/wt) | Example-3 Percent (wt/wt) | Example-4 Percent (wt/wt) | Example-5 Percent (wt/wt) |
| --- | --- | --- | --- | --- |
| Water | q.s. | q.s. | q.s. | q.s. |
| Glyceryl Stearate[1] | 4.03 | 4.24 | 3.84 | 4.24 |
| PEG-100 Stearate[1] | 3.89 | 4.09 | 3.71 | 4.09 |
| Cetearyl Alcohol[2] | 2.90 | 3.05 | 2.76 | 3.05 |
| Ceteareth-20[2] | 2.37 | 2.50 | 2.25 | 2.50 |
| Mineral Oil | 2.11 | 2.22 | 2.01 | 2.22 |
| Stearyl Alcohol | 1.59 | 1.67 | 1.51 | 1.67 |

-continued

| Ingredient | Example-2 Percent (wt/wt) | Example-3 Percent (wt/wt) | Example-4 Percent (wt/wt) | Example-5 Percent (wt/wt) |
|---|---|---|---|---|
| Dimethicone | 0.53 | 0.56 | 0.5 | 0.56 |
| Preservative[3] | 0.4–0.78 | 0.4–0.78 | 0.4–0.78 | 0.4–0.78 |
| Polyoxyethylene ether[4] | 5 | 5 | 5 | 5 |
| Urea | — | — | 5 | 5 |
| Vehicle total | 100% | 100% | 100% | 100% |
| DFMO[5] | 2–15%[5] | 2–15%[5] | 2–15%[5] | 2–15%[5] |

[1] Available as a blend, for example Cithrol GMS A/S ES0743 from Croda Chemical Company (UK)
[2] Available as a blend, for example Cosmowax EM5483 from Croda Chemical Company (UK)
[3] Preservative: combination of phenoxyethanol and methyl-, ethyl-, propyl- and butyl-parabens. The preservative is available as premixed blend or as individual ingredients.
[4] Polyoxyethylene ether may be selected from: ceteareth-20, ceteth-20, steareth-20, oleth-2, steareth-2, laureth-23, or laureth-4
[5] The active drug component DFMO is added at final levels of 2 to 15% to either the emulsified vehicle in examples 2–5, or is dissolved first in the water component and then the remaining ingredients are added to form a stable emulsion. After addition of DFMO the concentration of other ingredients in the vehicle are accordingly reduced. Preferably the DFMO is substantially optically pure L-DFMO.

EXAMPLE 6

Any one or more of the previous examples in combination with one or more of the following penetration enhancers: terpenes (3-hydroxy-3,7,11-trimethyl-1,6,10-dodecatriene or nerolidol), cis-9-octadecanoic acid (oleic acid), propan-2-ol, terpenes, cis-fatty acids (oleic acid, palmitoleic acid), acetone, laurocapram, dimethyl sulfoxide, 2-pyrrolidone, oleyl alcohol, glyceryl-3-stearate, cholesterol, myristic acid isopropyl ester, and propylene glycol. The penetration enhancer may be added at a concentration of, for example, 0.10% to 20%, or 0.5% to 12% by weight.

The composition should be topically applied to a selected area of the body from which it is desired to reduce hair growth. For example, the composition can be applied to the face, particularly to the beard area of the face, i.e., the cheek, neck, upper lip, or chin. The composition also may be used as an adjunct to other methods of hair removal including shaving, waxing, mechanical epilation, chemical depilation, electrolysis and laser-assisted hair removal.

The composition can also be applied to the legs, arms, torso or armpits. The composition is particularly suitable for reducing the growth of unwanted hair in women, particularly unwanted facial hair, for example, on the upper lip or chin. The composition should be applied once or twice a day, or even more frequently, to achieve a perceived reduction in hair growth. Perception of reduced hair growth can occur as early as 24 hours or 48 hours (for instance, between normal shaving intervals) following use or can take up to, for example, three months. Reduction in hair growth is demonstrated when, for example, the rate of hair growth is slowed, the need for removal is reduced, the subject perceives less hair on the treated site, or quantitatively, when the weight of hair removed (i.e., hair mass) is reduced (quantitatively), subjects perceive a reduction, for example, in facial hair, or subjects are less concerned or bothered about their unwanted hair (e.g., facial hair).

Skin Penetration Assay

An in vitro diffusion assay for vehicles was established based on that reported by Franz, Curr. Probl. Dermat. 7:58-68 (1978). Dorsal skin from Golden Syrian hamsters was clipped with electric clippers, trimmed to the appropriate size and placed in a diffusion chamber. The receptor fluid consisted of phosphate buffered saline, an isotonic solution for maintaining cell viability and 0.1% sodium azide, a preservative, and was placed in the lower chamber of the diffusion apparatus such that the level of the fluid was parallel to the mounted skin sample. After equilibration at 37° C. for at least 30 minutes, 10 μl or 20 μl of $^{14}$C-DFMO (0.5 to 1.0 1Ci per diffusion chamber) in a test or control formulation was added to the surface of the skin and gently spread over the entire surface with a glass stirring rod. Penetration of DFMO was assessed by periodically removing an aliquot (400 1L) throughout the course of the experiment, and quantitating using liquid scintillation.

This assay was conducted on the composition described in Example 1 using each of the polyoxyethylene ethers listed in Example 1. The vehicle not including a polyoxyethylene ether was used as a control. It was found that the vehicle including laureth-4 increased DFMO skin penetration 2.5 to 3-fold; the vehicle including oleth-2, 1.5 to 2-fold; the vehicle including laureth-23, about 1.5-fold; and the vehicle including steareth-20, about 1.5 to 2-fold.

Other embodiments are within the claims.

What is claimed is:

1. A method of reducing human hair growth, comprising selecting an area of skin from which reduced hair growth is desired, and
applying to the area of skin, in an amount effective to reduce hair growth, a composition including α-difluoromethylornithine and a dermatologically acceptable vehicle comprising at least 4% by weight of a polyoxyethylene ether having the chemical formula $R(OCH_2CH_2)_bOH$, where R is a saturated or unsaturated alkyl group including from 6 to 22 carbon atoms and b is from 2 to 200.

2. The method of claim 1, wherein the vehicle includes at least 6% of the polyoxyethylene ether by weight.

3. The method of claim 1, wherein R includes from 10 to 18 carbon atoms.

4. The method of claim 1, wherein b is from 2 to 50.

5. The method of claim 1, wherein the polyoxyethylene ether is steareth-2.

6. The method of claim 1, wherein the polyoxyethylene ether is oleth-2.

7. The method of claim 1, wherein the polyoxyethylene ether is laureth-4.

8. The method of claim 1, wherein the polyoxyethylene ether is laureth-23.

9. The method of claim 1, wherein the polyoxyethylene ether is ceteth-20.

10. The method of claim 1, wherein the polyoxyethylene ether is steareth-20.

11. The method of claim 1, wherein the polyoxyethylene ether is ceteareth-20.

12. The method of claim 1, wherein the α-difluoromethylornithine comprises at least about 80% L-α-difluoromethylornithine.

13. The method of claim 1, wherein the α-difluoromethylornithine is optically pure L-α-difluoromethylornithine.

14. The method of claim 13, wherein the composition includes from about 5% to about 15% by weight of the optically pure α-difluoromethylornithine, the vehicle includes at least 5% of the polyoxyethylene ether by weight, and the polyoxyethylene ether is ceteareth-20.

15. The method of claim 1, wherein the composition includes about 1% to about 20% of the α-difluoromethylomithine by weight.

16. The method of claim 1, wherein the composition includes about 5% to about 15% of the α-difluoromethylomithine by weight.

17. The method of claim 1, wherein the area of skin is on the face.

18. The method of claim 1, wherein the vehicle comprises at least 5% of the polyoxyethylene ether by weight.

19. A method of reducing human hair growth, comprising selecting an area of skin from which reduced hair growth is desired, and applying to the area of skin, in an amount effective to reduce hair growth, a composition including about 5% to about 15% by weight of α-difluoromethylomithine and a dermatologically acceptable vehicle comprising from 4% to about 6% by weight of a polyoxyethylene ether having the chemical formula $R(OCH_2 CH_2)_b OH$, where R is a saturated or unsaturated alkyl group including from 8 to 20 carbon atoms and b is from 2 to 50.

20. The method of claim 19, wherein the polyoxyethylene ether is selected from the group consisting of ceteareth-20, steareth-2, oleth-2, laureth-4, laureth-23, ceteth-20, and steareth-20.

21. The method of claim 19, wherein the vehicle comprises 4% of the polyoxyethylene ether by weight.

22. The method of claim 19, wherein the vehicle comprises about 5% of the polyoxyethylene ether by weight.

* * * * *

UNITED STATES PATENT AND TRADEMARK OFFICE
CERTIFICATE OF CORRECTION

PATENT NO. : 7,261,878 B2
APPLICATION NO. : 10/198456
DATED : August 28, 2007
INVENTOR(S) : Peter Styczynski, Gurpreet S. Ahluwalia and Douglas Shander It is certified that error appears in the above-identified patent and that said Letters Patent is hereby corrected as shown below:

In claim 12, lines 58-59, replace "α-difluoromethylomithine" with --α-difluoromethylornithine--.

In claim 12, lines 59-60, replace "α-difluoromethylomithine" with --α-difluoromethylornithine--.

In claim 15, lines 2-3, replace "α-difluoromethylomithine" with --α-difluoromethylornithine--.

In claim 16, lines 5-6, replace "α-difluoromethylomithine" with --α-difluoromethylornithine--.

In claim 19, line 16, replace "α-difluoromethylomithine" with --α-difluoromethylornithine--.

In claim 21, lines 11-12, after "comprises", insert --about--.

Signed and Sealed this

Nineteenth Day of August, 2008

JON W. DUDAS
*Director of the United States Patent and Trademark Office*

UNITED STATES PATENT AND TRADEMARK OFFICE
CERTIFICATE OF CORRECTION

PATENT NO. : 7,261,878 B2 Page 1 of 1
APPLICATION NO. : 10/198456
DATED : August 28, 2007
INVENTOR(S) : Peter Styczynski, Gurpreet S. Ahluwalia and Douglas Shander It is certified that error appears in the above-identified patent and that said Letters Patent is hereby corrected as shown below:

Column 6, In claim 12, lines 58-59, replace "α-difluoromethylomithine" with --α-difluoromethylornithine--.

Column 6, In claim 12, lines 59-60, replace "α-difluoromethylomithine" with --α-difluoromethylornithine--.

Column 7, In claim 15, lines 2-3, replace "α-difluoromethylomithine" with --α-difluoromethylornithine--.

Column 7, In claim 16, lines 5-6, replace "α-difluoromethylomithine" with --α-difluoromethylornithine--.

Column 7, In claim 19, line 16, replace "α-difluoromethylomithine" with --α-difluoromethylornithine--.

Column 8, In claim 21, lines 11-12, after "comprises", insert --about--.

This certificate supersedes the Certificate of Correction issued August 19, 2008.

Signed and Sealed this

Sixteenth Day of September, 2008

JON W. DUDAS
*Director of the United States Patent and Trademark Office*